United States Patent
Weiss et al.

(10) Patent No.: US 8,923,983 B2
(45) Date of Patent: Dec. 30, 2014

(54) DEVICE FOR REDUCING THE FAULT SUSCEPTIBILITY OF ELONGATED IMPLANTS

(75) Inventors: Ingo Weiss, Berlin (DE); Stefan Knorr, Berlin (DE); Michelle Maxfield, Berlin (DE); Michael Friedrich, Kleinmachnow (DE)

(73) Assignee: Biotronik CRM Patent AG, Baar (CH)

( * ) Notice: Subject to any disclaimer, the term of this patent is extended or adjusted under 35 U.S.C. 154(b) by 646 days.

(21) Appl. No.: 12/421,547

(22) Filed: Apr. 9, 2009

(65) Prior Publication Data

US 2009/0259281 A1    Oct. 15, 2009

(30) Foreign Application Priority Data

Apr. 14, 2008   (DE) .......................... 10 2008 018 990

(51) Int. Cl.
*A61N 1/00* (2006.01)
*A61N 1/05* (2006.01)
*A61N 1/08* (2006.01)

(52) U.S. Cl.
CPC *A61N 1/056* (2013.01); *A61N 1/05* (2013.01); *A61N 2001/086* (2013.01)
USPC .......................................................... 607/116

(58) Field of Classification Search
USPC ......................................... 607/112, 116–128
See application file for complete search history.

(56) References Cited

U.S. PATENT DOCUMENTS

| | | | | |
|---|---|---|---|---|
| 5,458,630 A * | 10/1995 | Hoegnelid et al. | ............ | 607/116 |
| 6,606,513 B2 * | 8/2003 | Lardo et al. | ................... | 600/411 |
| 7,463,933 B2 * | 12/2008 | Wahlstrom et al. | ........... | 607/126 |
| 7,822,484 B1 * | 10/2010 | Zhao et al. | .................... | 607/116 |
| 2003/0144719 A1 | 7/2003 | Zeijlemaker | | |
| 2004/0024425 A1 | 2/2004 | Worley et al. | | |
| 2005/0222658 A1 * | 10/2005 | Hoegh et al. | ................... | 607/116 |
| 2006/0106445 A1 * | 5/2006 | Woollett | ....................... | 607/122 |
| 2008/0167701 A1 * | 7/2008 | John et al. | ..................... | 607/116 |

FOREIGN PATENT DOCUMENTS

| | | |
|---|---|---|
| EP | 0 621 054 | 10/1994 |
| WO | WO 2006/055556 | 5/2005 |
| WO | WO 2006/097934 | 9/2006 |

OTHER PUBLICATIONS

European Search Report, dated Jun. 29, 2009.

* cited by examiner

*Primary Examiner* — Michael Kahelin
*Assistant Examiner* — Mallika D Fairchild
(74) *Attorney, Agent, or Firm* — ARC IP Law, PC; Joseph J. Mayo

(57) ABSTRACT

An implantable line having an elongated line body, a function conductor extending in the longitudinal direction of the line body, acting to implement a medical function of the line, whereby in addition to the function conductor, a field decoupling conductor which extends over at least a section of the length of the line body essentially parallel to the function conductor is provided, thereby reducing the coupling of the function conductor to an external field.

7 Claims, 13 Drawing Sheets

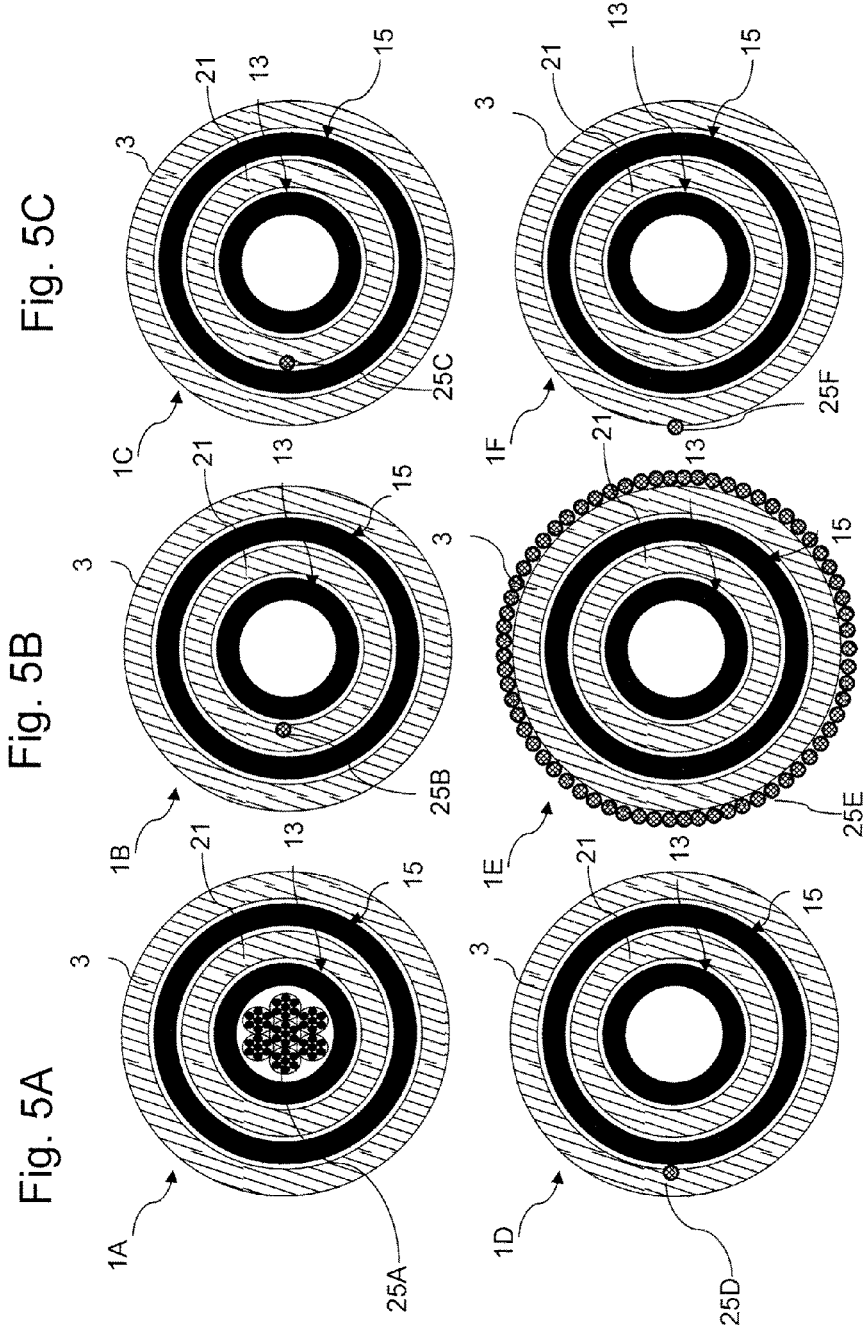

DEVICE FOR REDUCING THE FAULT SUSCEPTIBILITY OF ELONGATED IMPLANTS

This application takes priority from German Patent Application DE 10 2008 018 990.1, filed 14 Apr. 2008, the specification of which is hereby incorporated herein by reference.

BACKGROUND OF THE INVENTION

1. Field of the Invention

The invention relates to an implantable line having an elongated line body and a function conductor extending in the longitudinal direction of the line body, acting to implement a medical function of the line. Such lines are in particular stimulation electrode lines (hereinafter also referred to as "electrodes") of heart pacemakers or shock electrode lines of implantable defibrillators but also catheters containing an elongated conductive structure.

2. Description of the Related Art

Medical implants such as the pacemakers and defibrillators mentioned above often form an electric connection inside the patient's body. Such a connection serves to measure electric signals and/or to stimulate body cells. This connection is often embodied as an elongated electrode. At the present time, electric signals are transmitted between the implant and the electrode contacts, which include but are not limited to tips, rings, HV shock coils and sensors with materials that are good conductors.

If a system comprising an implant and an electrode is exposed to strong interference fields such as EMI or MRI, unwanted malfunctions may occur, specifically resulting in heating of parts of the system or electric malfunctions (e.g., resets). The heating may cause damage to body tissues or even organs if the heated parts are in direct contact with the tissue. This is the case with the electrode tip in particular.

The cause of the unwanted malfunction is the interaction of the field with the elongated line structure of the electrode. The electrode acts as an antenna that receives energy from the surrounding fields. This energy on the lines being used therapeutically can be delivered by the antenna proximally to the implant or distally to the tissue via the electrode contacts.

The same problems also occur with other elongated conductive structures whose proximal end is not necessarily connected to an implant (e.g., in the case of catheters, temporary electrodes, etc.).

BRIEF SUMMARY OF THE INVENTION

The object of the present invention is to make available an improved implantable line of the aforementioned type which has improved properties in strong external fields.

This object is achieved by an implantable line having the features of at least the independent claim made herein. Expedient refinements of the inventive idea are the subject matter of the dependent claims.

An important object of the present invention is to reduce the influence of strong external fields by providing an additional conductive element in the implantable line. The additional conductors, so-called field decoupling conductors, alter the interaction between the external field and the line in such a way that a different electric current distribution develops on the line. The inadvertent antenna properties of the line change as a result of this detuning. This results in less heating of the distal line contacts. This advantage applies to various geometric shapes and various positions of the line.

This modification is fixedly installed in the line or is retrofittable. As a result, the antenna property of the line is exacerbated and the surrounding tissue is not heated so much. With a retrofittable modification, heating of the electrode(s) can be reduced in particular in the case of lines that have already been implanted.

According to the preceding discussion, this invention can be applied especially advantageously in an electrode line having at least one electrode and one electrode terminal contact at one end of the line, whereby the function conductor connects the electrode to the electrode terminal contact, and the field decoupling line does not have any galvanic coupling with the function conductor in the area of the/each electrode.

The proximal end of the field decoupling conductor is not necessarily connected to the connected (implanted) device and/or its function units, which implement the relevant medical function via the function conductor. However, such a connection may easily exist if the additional terminal of the field decoupling conductor can support or at least does not impair the medical function.

In an inexpensive and expedient embodiment, the field decoupling conductor has a metal wire or a metal strip and/or the means provided in the line for inserting or applying a field decoupling conductor having a metal wire or a metal strip are adapted. In an alternative embodiment, the field decoupling conductor has an elongated conductive polymer structure or a conductive liquid in a conductor channel (interior lumen of the line body).

If the field decoupling conductor is made of a metal or a polymer, a multi-strand design and in particular a multi-strand cable structure may optionally be advantageous for mechanical reasons. In addition, the field decoupling conductor may have a helical, meandering, folded or self-similar fine structure, which is optionally inserted into a corresponding fine structure of the function conductor or is designed around a defined structure of the function conductor.

In another embodiment, the field decoupling conductor and/or the function conductor is designed as a metal deposit on an insulating substrate whereby in particular the field decoupling conductor and the function conductor are insulated from one another on one and the same substrate. Specifically, the substrate here may be made of flexible tubing. Such a flexible substrate, which is advantageous from the standpoint of easy implantation in the body, may easily be provided with a sufficiently thick conductor layer using modern deposition techniques.

From the standpoint of various application aspects and with regard to special electric and mechanical requirements of the line improved according to the present invention in particular, a variety of other embodiments and/or modifications of this concept are possible.

The field decoupling conductor may thus use several partial pieces which have different electric and/or mechanical properties and/or insulation of the field decoupling conductor may be inhomogeneous or its properties may change over the length. One or both ends of a field decoupling conductor system consisting of multiple conductors may be electrically connected to one another at one or both ends, or partial pieces of a subdivided structure may be electrically interconnected, optionally via discrete components (resistors, capacitors, inductors) through conductive or dielectric materials (plastics, metals, ceramics), semiconductor structures, nonlinear components or even sensors (such as thermocouples, thermistors, field strength sensors for electric or magnetic fields, etc.). In special embodiments, a connection via special components which have a giant magnetoresistance (GMR), an anisotropic magnetoresistance (AMR), a colossal magnetoresistance (CMR) or a tunnel magnetoresistance (TMR) is also possible.

In a construction comprising multiple partial pieces, they may optionally form an electric oscillating circuit whose parameters may be coordinated with the field parameters of an external field that acts in a predetermined manner in the use state.

In a conductive embodiment, the proximal end may be in contact with at least one of the contacts of a proximal electrode plug (tip or ring contact) or with a metal surface which is part of an implant, but may be insulated from the remaining housing if necessary. The connection to the proximal end may also include one or more passive or active electronic components. The proximal end of the field decoupling conductor may also be designed to be conductive even when not connected to a respective medical implant; on the other hand, however, a proximally insulated embodiment is to be preferred for certain applications.

To impart suitable mechanical properties to the proposed line, it is possible to provide for the distal region of the field decoupling conductor to be particularly flexible, for example, due to a suitable choice of material, geometry and optionally insulation in order to avoid an unwanted stiffening of the distal area of the line on the whole. The embodiment already mentioned above using a liquid conductor (or consisting exclusively of liquid conductors), in particular in an extremely flexible tubing, is also advantageous in this sense. Such highly flexible tubing having a thin metallized layer at the surface also has similar advantageous properties.

Also advantageous from a mechanical standpoint and from the standpoint of implantation technology is an embodiment of the field decoupling conductor in which its surface has a low coefficient of friction, e.g., is provided with a PTFE coating or the like.

In a special embodiment, the proximal end of the field decoupling conductor may have an elastic section or a corresponding component (e.g., lamellae, coils, etc.) to also reliably establish electric contact with an adjacent conductor—e.g., in a standard connector with an extra contact—even under alternating mechanical loads.

For rapid differentiation of inventive lines from traditional lines, a suitable X-ray or ultrasonic marker or some other marking which is clearly visible in an imaging process may be provided.

In an embodiment that is preferred from today's standpoint, the field decoupling conductor is or may be arranged within the body of the line. Essentially, however, the field decoupling conductor is or may be attached to the outside of the line body. It is self-evident that it is preferable to install the field decoupling conductor in the line body especially in the case of extremely long lines. However, a subsequent attachment of the field decoupling conductor from the outside may also be possible and advantageous, specifically for subsequent improvement of interfering field performance of existing lines that are not excessively long or that are in a noncritical range from the standpoint of implantation.

In another embodiment of the present invention, insulation means for insulating the field decoupling conductor from the function conductor and/or the/each electrode are provided in the interior of the line body, or a field decoupling conductor provided for subsequent insertion or attachment has an integral insulation.

Additional embodiments are possible for a field decoupling structure installed in the line as follows:

a line structure which, together with a line that is used therapeutically and/or for measurement technology, is wound as a coil (e.g., in the helix of the internal conductor);

a line structure that is guided or coiled parallel to and as close as possible to physical contact (but not galvanic) with a line that is used therapeutically and/or for measurement technology (e.g., around the helix of the internal conductor, around the helix of the external conductor or around a cable);

a line structure which is partially wound around the wire of the helix of a line used therapeutically and/or for measurement technology;

a line structure whose design is at least partially self-similar, so that a long electric line can be accommodated in a short structure;

a line structure which is inside the electrode (eccentric or centered) or is outside the electrode (coaxial, eccentric);

for which an embodiment as a "retrofittable" field decoupling structure provided as the second fundamental embodiment is possible;

which can be shortened to the required length (depending on the length of the respective electrode);

which can be plugged onto an insertion aid and thus can be inserted more easily into the lumen of an electrode, which may be embodied as tubing, for example, into whose interior lumen a mandrel can be inserted;

which may be shortened proximally and/or distally;

which has a special shape proximally, so that it can be removed from the interior lumen of the electrode by using a suitable tool (e.g., for repositioning the electrode with a mandrel);

which is made partially of a material, e.g., metal or plastic whose flexibility increases with an increase in temperature (so the structure to be inserted is initially rigid and becomes softer on reaching body temperature—the stiffening of the electrode is minor);

which uses several conductors joined together at several locations (this connection ensures a stiffening with respect to the same conductor arrangement without the connection. The connection can be released subsequently, e.g., by dissolving the bonding substance. The rigidity of the line structure can thus be reduced after insertion into the interior lumen of an electrode by, for example, injecting water to dissolve the salt crystals which bond the wires of a cable);

which can be fixedly secured in the interior lumen of the electrode to prevent displacement and possible perforation of tissue (especially in the case of coronary sinus electrodes having a continuous distal lumen opening), which uses a gel;

which uses a two-component curable plastic;

which uses a conductive liquid that is injected directly into the interior lumen of the electrode. In this case, there is electric contact with the electrode tip as well as with the internal helix;

whereby the injection of the liquid conductor is accomplished with a long tube that is inserted initially into the distal end of the lumen.

One alternative to the distally insulated line structure is a distally uninsulated line structure, which is pushed into an electrode whose distal end is insulated on the inside. This insulation can be ensured by a dielectric material that is fixedly incorporated into the electrode or is applied subsequently to it (e.g., during implantation).

Providing an additional field decoupling structure in a medical line according to the present invention allows the construction of MR-safe implants, which have only moderate heating of the electrode tip even when exposed to a strong electromagnetic field (e.g., during an MRI examination). It also allows subsequent modification of electrodes already implanted to obtain an MR-safe system, in particular comprising lines that are in the body but are not connected to an active implant so they are unused.

BRIEF DESCRIPTION OF THE DRAWINGS

Advantages and expedient features of the invention are also derived from the following description of specific embodiments on the basis of the figures, in which:

FIGS. 5A and 5F show schematic cross-sectional diagrams of inventive bipolar stimulation electrode lines in which the field decoupling conductor has various embodiments and/or positions;

DETAILED DESCRIPTION OF THE INVENTION

Figure 1A:
FIGS. 1A to 1D show an overall view of two detailed views (distal and proximal sections) of a stimulation electrode line according to two embodiments of the invention.
Figure 1B:
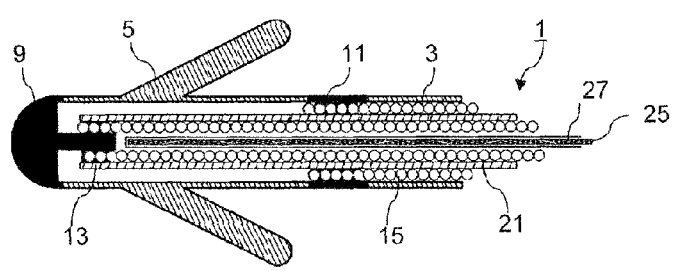
Figure 1C:
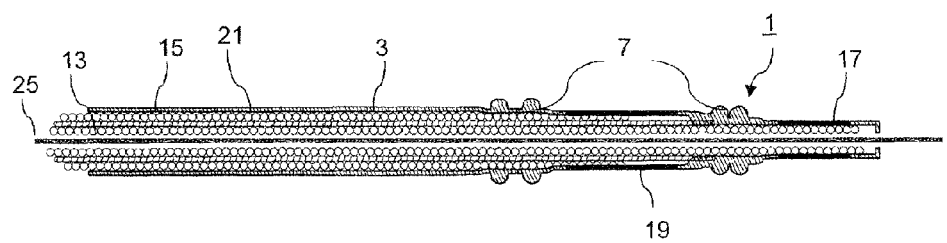
Figure 1D:
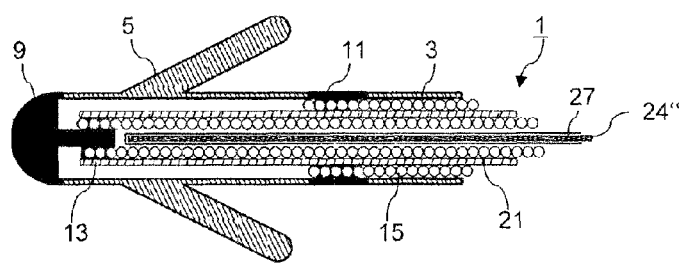

FIGS. 1A to 1D show an inventive stimulation electrode arrangement 1 in schematic longitudinal sectional diagrams, namely an overall view (FIG. 1A) and detailed views of the distal part (FIG. 1B) and the proximal part (FIG. 1C). along with second embodiment shown in FIG. 1D, (also see FIG. 12) The electrode line comprises a line body 3 on which fins 5 are integrally molded close to the distal end 2 for anchoring as a stimulation electrode line in the trabecular meshwork of the heart and sealing lips and/or sealing rings 7 for fluid-tight sealing in an IS1 connector of a stimulation device (heart pacemaker) close to the proximal end. An essentially hemispherical tip electrode 9 is incorporated as the distal end in the line body 3 and a ring electrode 11 is incorporated proximally and at a distance thereto.

The electrodes 9, 11 are connected via an internal and external electrode feeder lines 13 and 15, respectively, arranged coaxially and/or coiled, said feeder line(s) being connected at the proximal end of the line to a first and a second plug connection contact 17 and 19, respectively. The electrode feeder lines 13, 15 are insulated from one another by an insulation tubing 21. They serve as function conductors of the electrode line 1. An additional elongated line 25 having an insulation material 27 which has the function of the field decoupling conductor already explained above runs in the longitudinal axis thereof, and which does not contact any electrode as shown. In addition, as shown in FIG. 1D, conductive liquid 24" is utilized as the field decoupling conductor.

Figure 2:
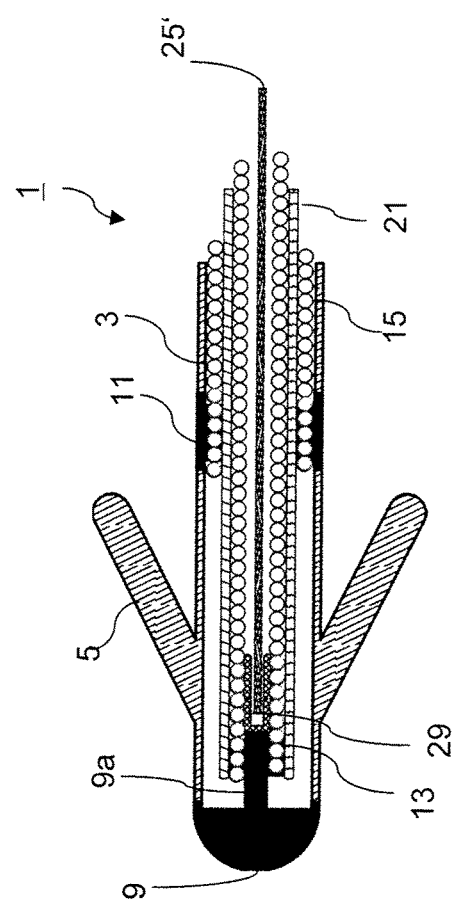
FIG. 2 shows a detailed view of the distal section of a modified embodiment of the electrode line.

The modified electrode line 1 shown as a detail view in FIG. 2 has essentially the same structure as the electrode line 1 according to FIGS. 1A to 1C, which is also labeled with the same reference numerals to this extent. It differs from the latter in the uninsulated central field decoupling conductor 25' and the fact that an insulating sleeve 29 is additionally provided inside the distal end section of the internal electrode feeder line 13 in contact with a pin-type inwardly directed protrusion 9a of the tip electrode 9. This sleeve fundamentally allows the use of an uninsulated wire as a field decoupling conductor without a low-impedance connection between the latter and the tip electrode.

Figure 3:
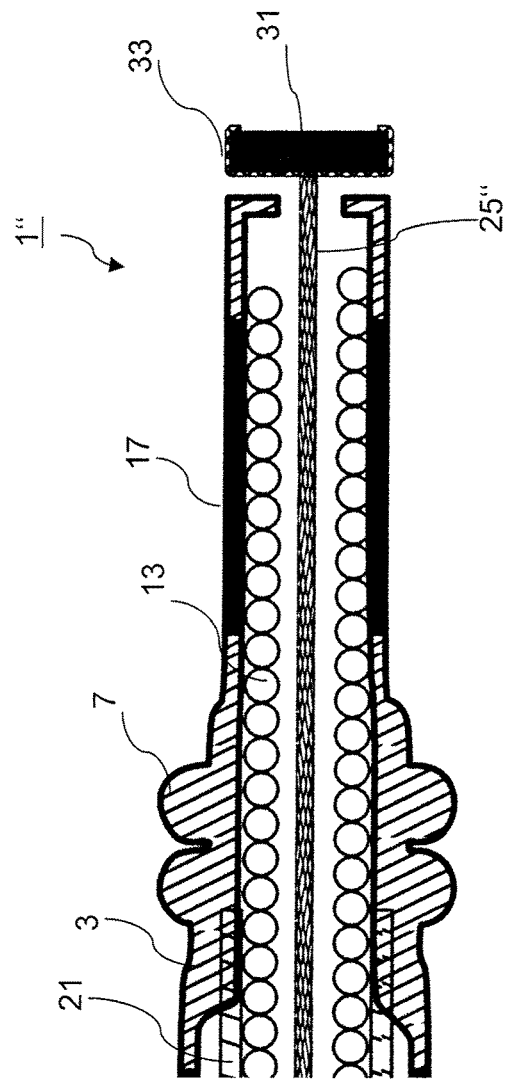
FIG. 3 shows a detailed view of the proximal end of another embodiment of the inventive electrode line.

In another modified electrode line 1" which is illustrated in FIG. 3 and which corresponds to the other parts of the electrode line 1 from FIGS. 1A to 1C, the central field decoupling conductor 25" on the proximal end has a circular connecting plate 31, as seen in a view from above, its circumference and an end face being covered with an insulating coating 33 except for the contact area with the field decoupling conductor 25".

Figure 4C:
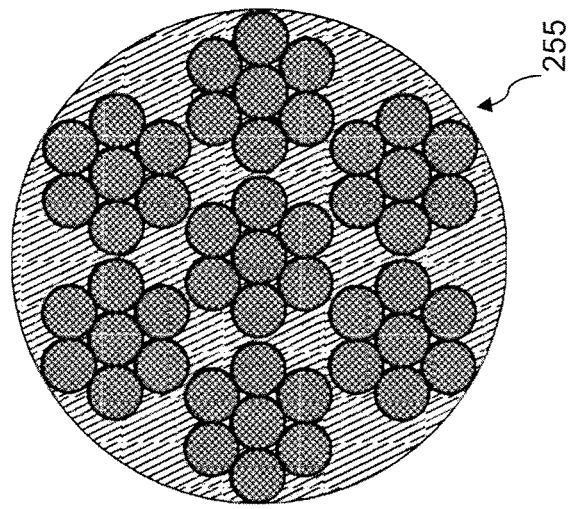
FIGS. 4A to 4C show cross-sectional diagrams of different embodiments of the field decoupling conductor of an inventive stimulation electrode line.
Figure 4B:
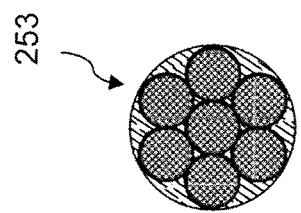
Figure 4A:
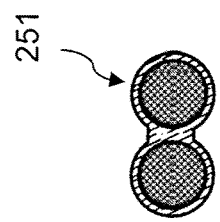

FIGS. 4A to 4C show a two-stranded line 251, a seven-stranded cable 253 and a braided 7×7 cable 255 as different embodiments of a field decoupling conductor, each shown with insulation (not labeled separately). The cables may be constructed inhomogeneously within themselves, and they optionally have a core of a different material than the remaining strands.

FIGS. 5A to 5F show various superstructures of inventive stimulation electrode lines 1A to 1F, each of which contains the traditional components—line body 3, internal feeder line 13, external feeder line 15 and insulation tubing 21. With line 1A, a multi-stranded cable structure 25A is provided as the field decoupling conductor in a central lumen (not labeled separately) and in the case of lines 1B (FIG. 5B), 1C (FIG. 5C), 1D (FIG. 5D) and 1F (FIG. 5F), a single wire 25B or 25C or 25D or 25F is provided eccentrically in each in various positions with regard to the internal and external feeder lines and/or externally on the line body 3. The line 1E according to FIG. 5E has a multi-stranded field decoupling jacket conductor 25E surrounding the entire circumference of the line body 3.

Figure 6:
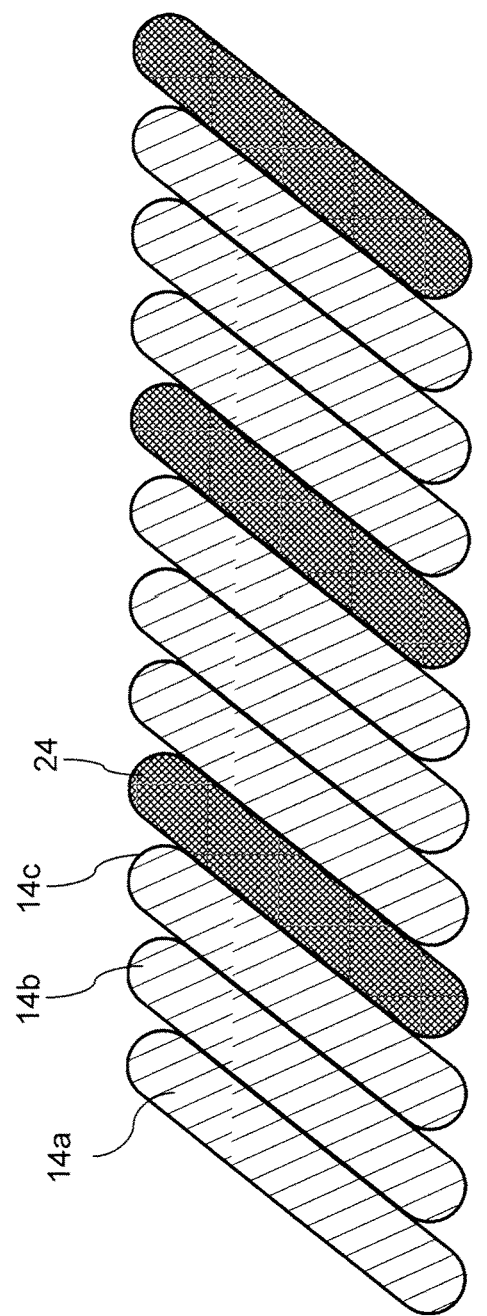
FIGS. 6 to 8 show schematic diagrams of other embodiments and/or arrangements of the field decoupling conductor.
Figure 7:
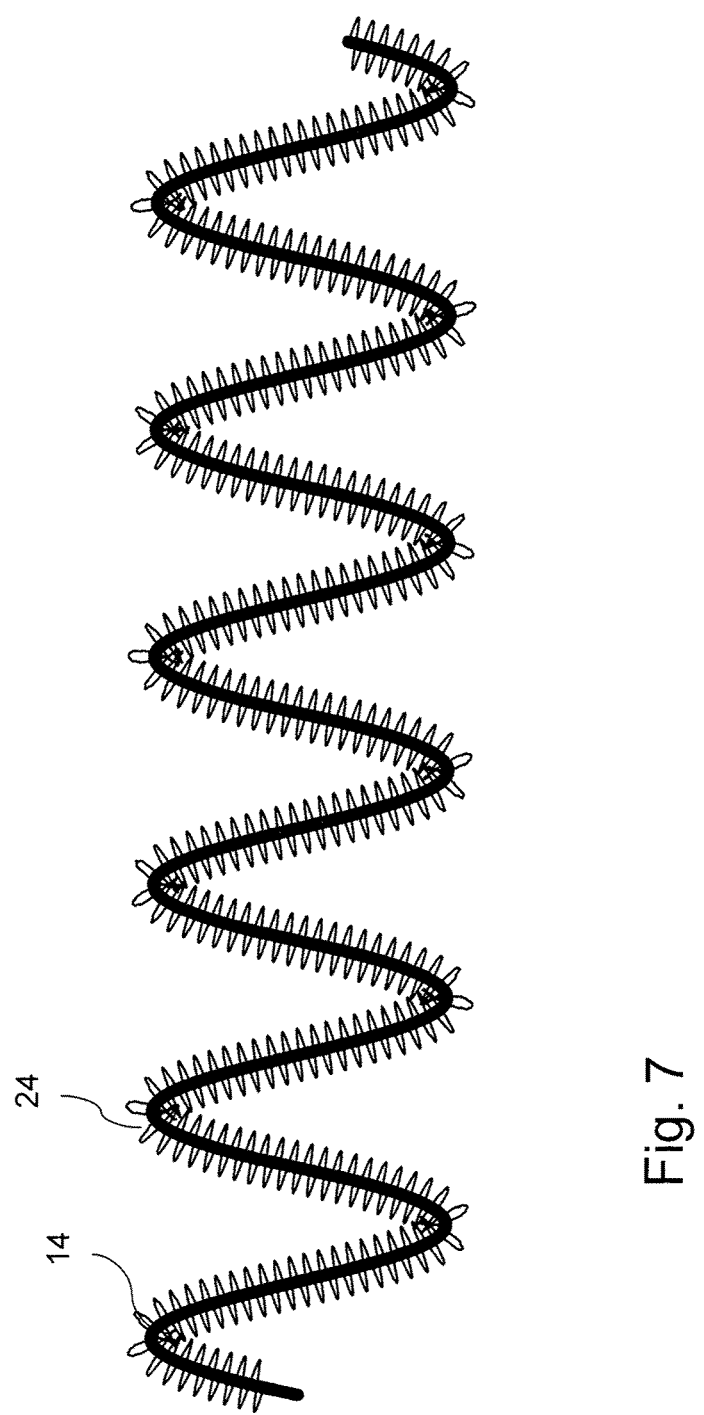

The field decoupling conductor may have a helical, meandering, folded or self-similar structure on the whole or in part and may also be coiled jointly with the function conductors in a multi-stranded helix, for example, as shown in FIG. 6, where a four-stranded helix of three function conductors 14a to 14c and one field decoupling conductor 24 is coiled up. In the additional embodiment shown in FIG. 7, a field decoupling conductor 24 is coiled as a helix around a line (function conductor 14) which is in turn also coiled and is used therapeutically.

Figure 8:
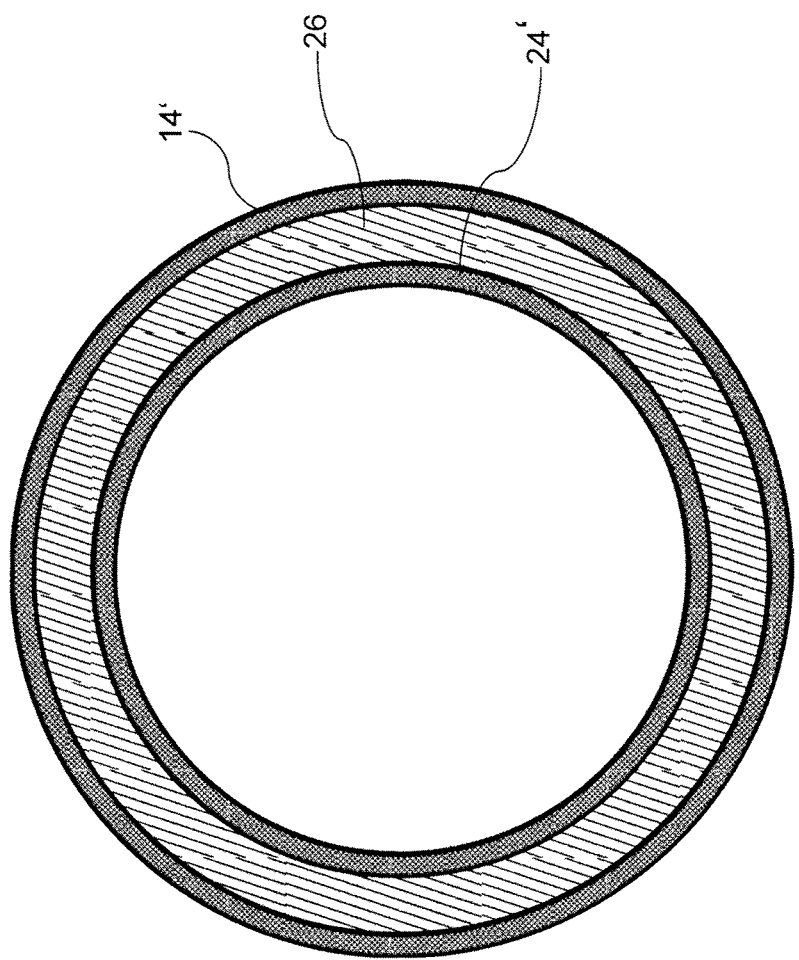

As an additional embodiment, FIG. 8 shows a line structure consisting of thin metal layers on both sides of a substrate, namely in the form of an insulating tubing 26 with an outer coating 14' that serves as the function conductor and an inner coating 24' that serves as the field decoupling conductor. In modified embodiments, the function assignment of the conductive layers may also be reversed or the tubing may on the whole represent only a two-layer field decoupling conductor.

Figure 9A:
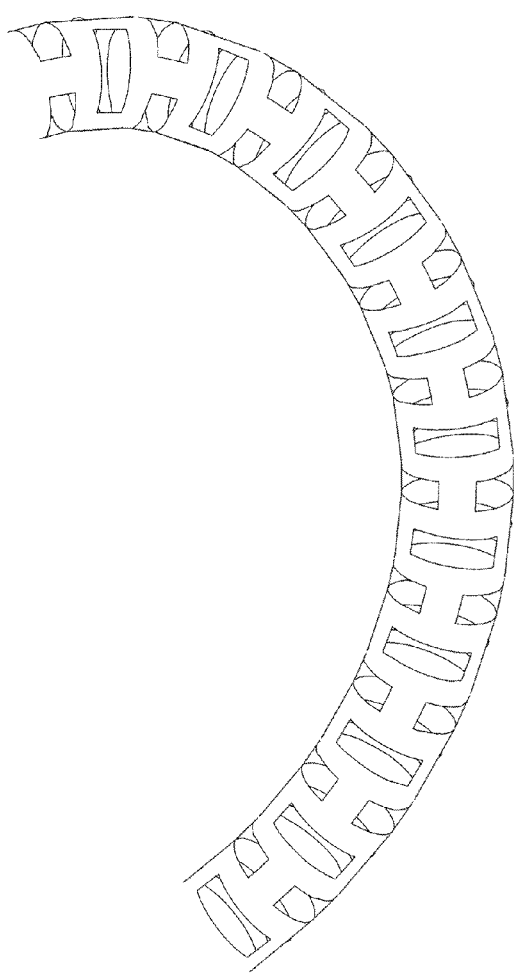
FIGS. 9A and 9B show a perspective detail diagram as well as a schematic perspective detailed view of another embodiment of the field decoupling conductor.
Figure 9B:
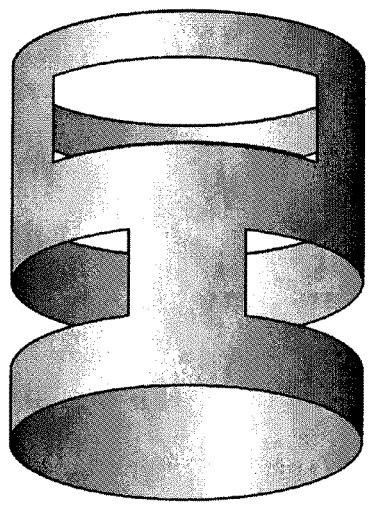
Figure 10A:
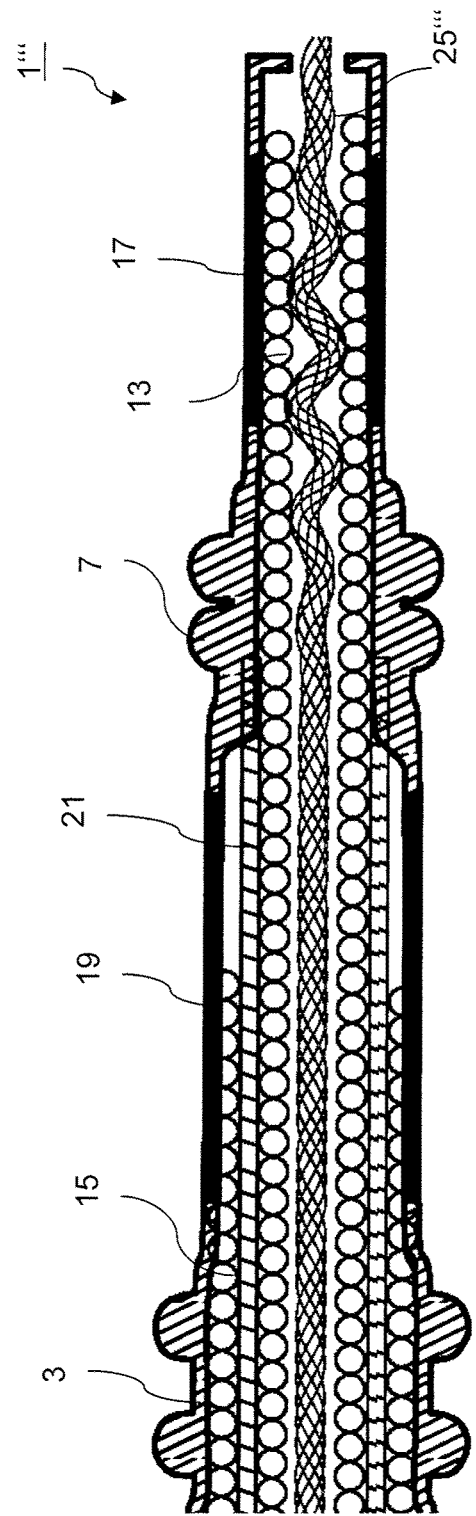
FIG. 10 shows a schematic longitudinal sectional diagram of the proximal section of another inventive stimulation electrode line.

The metallization may have a fine structure, which is created by a lithographic process, for example. The carrier of the metallization may be a helix or may have some other fine structure. The carrier should be very elastic due to its shape, so as not to excessively increase the rigidity of the electrode. The rigidity of a tubing can be varied, e.g., by means of multiple recesses, e.g., by incisions which greatly reduce the planar moment of inertia of the structure without greatly influencing the longitudinal rigidity. FIGS. 9A and 9B show an exemplary embodiment of such a tubular structure with mutually offset, periodically recurring sections.

A tubular structure can be inserted easily with a guide wire into the internal lumen of the electrode even if it has a low intrinsic rigidity. On the distal end, a structure may be provided which, together with another fitting structure in the interior of the electrode, forms a retaining mechanism. On insertion of the tubing with a guide wire, the tubing is held in the tip and the guide wire can be removed without altering the position of the tubing. The retaining mechanism should be releasable to allow removal of the field decoupling conductor.

As another modification of the embodiment illustrated in FIGS. 1A to 1C, FIG. 10 shows an electrode line 1''' in the interior of which runs a field decoupling conductor 25''' with a coiled proximal section that establishes the desired electric contact with the internal feeder line 15.

Figure 11A:
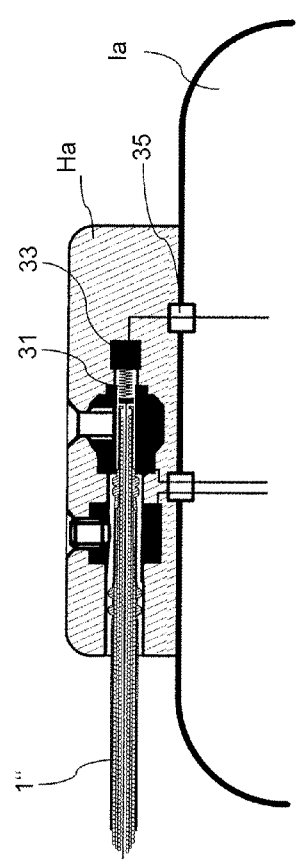
FIGS. 11A to 11C show schematic diagrams of different embodiments of the stimulation device terminal of inventive stimulation electrode lines.
Figure 11B:
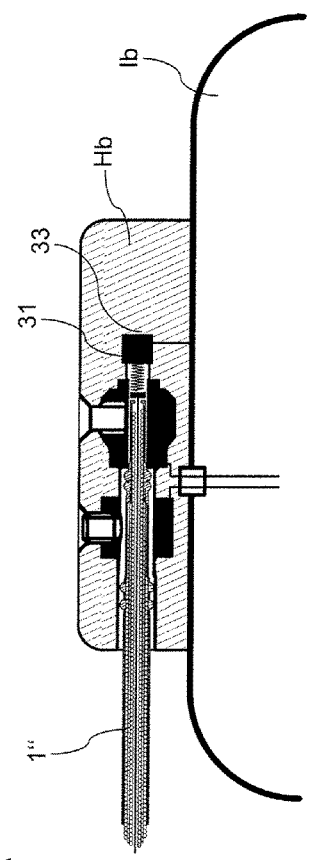
Figure 11C:
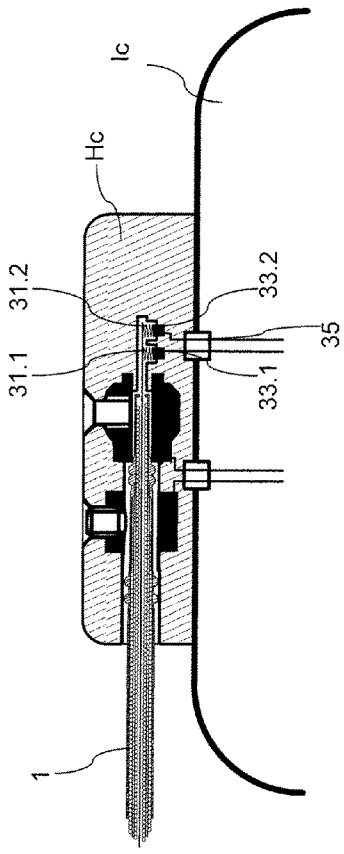

FIGS. 11A to 11C illustrate schematically different variants of the connection of an inventive electrode line 1'' according to FIG. 3 and/or a line 1 according to FIG. 1 on a medical implant. The implants Ia, Ib and/or Ic shown here differ in the design of their respective headers Ha, Hb and/or Hc. The connectors are each based on and compatible with the IS1 standard but offer the additional possibility of contacting a field decoupling conductor of the electrode line.

FIG. 11A shows an implant 1a having a header Ha, which electrically connects the field decoupling conductor to a contact 33 provided for this purpose via a compression spring 31, whereby a housing feed-through 35 continues the contact into the interior of the housing of the implant. FIG. 11B illustrates a similar embodiment in which the housing feed-through is omitted, however, and the field decoupling conductor is connected directly to the implant housing via the contact 33. As shown in FIG. 11C, separate contacting of multiple individual conductors of a field decoupling conductor structure is also possible, namely via separate contact springs 31.1, 31.2 and contacts 33.1, 33.2 in the header Hc.

Figure 12:
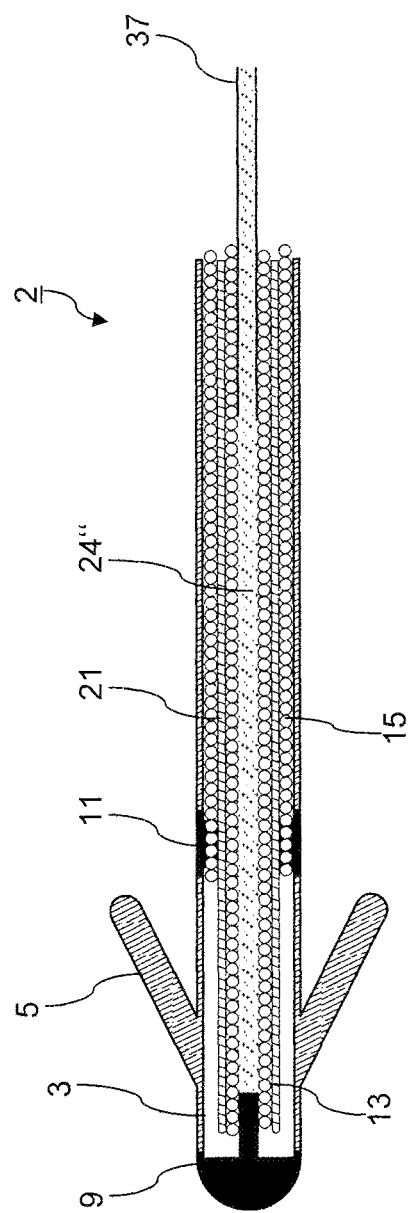
FIG. 12 shows a schematic longitudinal sectional diagram of another embodiment of the inventive stimulation electrode line in a phase of its manufacture.

A special embodiment of the field decoupling conductor as illustrated in FIG. 12 uses a conductive liquid, which can be injected into the internal lumen of the electrode. This liquid may be an aqueous solution of salts, for example. To achieve good longitudinal conductivity of the liquid column, it should extend from the distal end to the proximal end without interruption (e.g., air bubbles). This can be accomplished, for example, by means of an injection through a long tube, the tube being guided into the electrode tip and then being withdrawn from the interior lumen during the injection. FIG. 12 shows a corresponding electrode line 2, whose structure corresponds largely to that of the electrode line 1 from FIGS. 1A to 1D and which is also labeled with the same reference numerals to this extent. The difference is that instead of a metallic central field decoupling conductor in the interior lumen, a conductive liquid 24'' is provided, the liquid being introduced subsequently through a tube 37 into the electrode line, which has already been positioned.

To keep the conductivity of the solution constant over time, diffusion of the ions out of the electrode should take place very slowly. This can be guaranteed through suitable barrier layers or sufficiently large ions.

To facilitate the insertion of the field decoupling conductor, a rigid structure is desirable. The field decoupling conductor that has been put in position should, however, have the lowest possible rigidity. Both goals can be achieved if the rigidity is variable. This can be accomplished, e.g., by using materials having a so-called memory effect.

Figures 13A, 13B:
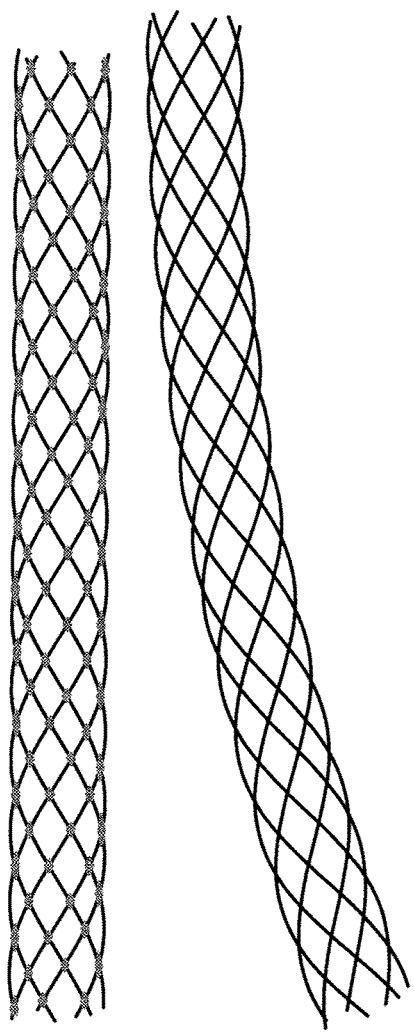
FIGS. 13A and 13B show schematic diagrams of another structural embodiment of the field decoupling conductor.

Alternatively, multiple partial structures of the field decoupling conductor can be stiffened with a soluble substance which dissolves after implantation. This reduces rigidity. As an example, FIGS. 13A and 13B show a braided cable, whose individual fibers may use different materials. The individual fibers are joined by means of sugar crystals or salt crystals, for example, which can be dissolved with water after implantation. FIG. 13A shows the rigid mesh prior to implantation with the stiffening reinforcements, and FIG. 13B shows the flexible mesh with the dissolved stiffening elements.

The embodiment of the invention is not limited to the examples described here and the aspects that have been emphasized here, but instead a number of modifications which are within the scope of technical expertise are possible.

What is claimed is:

1. An implantable line (1) comprising:
   an elongated line body;
   at least one electrode comprising
      a tip electrode and a ring electrode and
      a first and second electrode terminal contact at opposing ends of the elongated line body;
   a first and second function conductor (13, 15) which extend in a longitudinal direction of the elongated line body that implement a medical function of the implantable line;
   wherein the first and second function conductor (13, 15) connect the tip electrode and the ring electrode to the first and second electrode terminal contact respectively;
   a field decoupling conductor (24'') which extends at least between said at least one electrode to said first and second electrode terminal contact wherein said field decoupling conductor (24'') reduces coupling of the function conductor (13, 15) to an external field wherein said field decoupling conductor is configured to terminate at a proximal end of said elongated line body within a header of an implantable medical device wherein said field decoupling conductor is a conductive liquid configured with a volume of liquid to decouple the function conductor (13, 15) to an external field; and,
   wherein said field decoupling conductor that is said conductive liquid does not electrically couple said at least one electrode comprising said tip electrode and said ring electrode to said first or said second electrode terminal contact.

2. The implantable line according to claim 1, further comprising:
   a lumen in which to insert or apply the field decoupling conductor (24'').

3. The implantable line according to claim 1, wherein the field decoupling conductor (24'') is inside the elongated line body.

4. The implantable line according to claim 2, further comprising:
   wherein the field decoupling conductor (24'') is configured for subsequent insertion or application in a previously implanted elongated line body via injection from a tube that is inserted into said lumen with said conductive liquid and then withdrawn from said lumen without said conductive liquid, therein leaving said conductive liquid within said previously implanted elongated line body.

5. The implantable line according to claim 1 wherein said conductive liquid is an aqueous solution of salts.

6. The implantable line according to claim 1 wherein said conductive liquid comprises large ions.

7. A method of implementing the implantable line (1) comprising:
- providing the implantable line of claim 2;
- inserting a tube into the lumen with said conductive liquid;
- inserting said conductive liquid into said internal lumen using said tube; and,
- withdrawing said tube from said internal lumen without said conductive liquid.

* * * * *